United States Patent [19]

Berg

[11] Patent Number: 4,925,533
[45] Date of Patent: May 15, 1990

[54] SEPARATION OF VINYL ACETATE FROM ETHYL ACETATE BY EXTRACTIVE DISTILLATION WITH ACIDS OR ACID AMIDES

[75] Inventor: Lloyd Berg, 1314 S. Third Ave., Bozeman, Mont. 59715

[73] Assignee: Lloyd Berg, Bozeman, Mont.

[21] Appl. No.: 319,166

[22] Filed: Mar. 6, 1989

[51] Int. Cl.$^5$ .......................... B01D 3/40; C07C 67/54
[52] U.S. Cl. ........................................ 203/51; 203/56; 203/58; 203/60; 203/61; 203/62; 203/64; 203/DIG. 10; 560/248
[58] Field of Search .................... 560/248; 203/51, 61, 203/60, 56, 64, 58, 62, DIG. 10

[56] References Cited

U.S. PATENT DOCUMENTS

| | | | |
|---|---|---|---|
| 3,458,406 | 7/1969 | Fisher et al. | 203/44 |
| 3,591,463 | 7/1971 | Copelin | 203/71 |
| 3,691,021 | 9/1972 | Feldman | 203/65 |
| 3,736,236 | 5/1973 | Di Fiore et al. | 203/51 |

FOREIGN PATENT DOCUMENTS

| | | | |
|---|---|---|---|
| 2132299 | 1/1972 | Fed. Rep. of Germany | 203/34 |
| 47-13494 | 4/1972 | Japan | 203/61 |

*Primary Examiner*—Wilbur Bascomb

[57] ABSTRACT

Vinyl acetate cannot be easily removed from ethyl acetate by distillation because of the closeness of their boiling points. Vinyl acetate can be readily separated from ethyl acetate by means of extractive distillation. Typical effective agents are formic acid, formamide and formic acid-formamide mixture.

2 Claims, No Drawings

SEPARATION OF VINYL ACETATE FROM ETHYL ACETATE BY EXTRACTIVE DISTILLATION WITH ACIDS OR ACID AMIDES

This invention relates to a method for separating vinyl acetate from ethyl acetate using certain acids or acid amides as the agents in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with lowest boiling component. This usually requires that the extractive agent boil twenty Centigrade degrees or more than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Vinyl acetate and ethyl acetate boil only four Celcius degrees apart and thus have a relative volatility of only 1.08. Table 1 shows the relationship between relative volatility and plate requirements for rectification. With its relative volatility of only 1.08, the separation of vinyl acetate from ethyl acetate in 99% purity requires 160 plates of 75% efficiency. If a method could be found to increase the relative volatility to 1.7, the plate requirement would be only 23. Extractive distillation would be an attractive method of effecting the separation of vinyl acetate from ethyl acetate if agents can be found that (1) increase the relative volatility of vinyl acetate to ethyl acetate and (2) are easy to recover from ethyl acetate, that is, form no azeotrope with ethyl acetate and boil sufficiently above ethyl acetate to make separation possible with only a few theoretical plates.

TABLE 1

| Rectification Column Plates Required for 99% Separation | |
|---|---|
| Relative Volatility | Plates, 75% Efficiency |
| 1.08 | 160 |
| 1.2 | 68 |
| 1.35 | 42 |
| 1.6 | 26 |

TABLE 1-continued

| Rectification Column Plates Required for 99% Separation | |
|---|---|
| Relative Volatility | Plates, 75% Efficiency |
| 1.7 | 23 |

Extractive distillation typically requires the addition of an equal amount to twice as much extractive agent as vinyl acetate-ethyl acetate on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with ethyl acetate, otherwise it will form a two-phase azeotrope with the ethyl acetate in the recovery column and some other method of separation will have to be employed.

OBJECTIVE OF THE INVENTION

The object of this invention is to provide a process or method of extractive distillation that will enhance the relative volatility of vinyl acetate from ethyl acetate in their separation in a rectification column. It is a further object of this invention to identify organic compounds which are stable, can be separated from ethyl acetate by rectification with relatively few plates and can be recycled to the extractive distillation column and reused with little decomposition.

SUMMARY OF THE INVENTION

The objects of the invention are provided by a process for separating vinyl acetate from ethyl acetate which entails the use of certain acids or acid amides, either alone or admixed, as the agent in extractive distillation.

TABLE 2

Effective Extractive Distillation Agents for Vinyl Acetate-Ethyl Acetate Separation

| Compounds | Ratio | Relative Volatility |
|---|---|---|
| None | — | 1.08 |
| Formic Acid | 1 | 1.58 |
| Formic Acid, Formamide | ½:½ | 1.72 |
| Formic Acid, Acetophenone | ½:½ | 1.43 |
| Formic Acid, Adiponitrile | ½:½ | 1.30 |
| Formic Acid, Sulfolane | ½:½ | 1.23 |
| Formic Acid, Acetamide | ½:½ | 1.17 |
| Propionic Acid | 1 | 1.22 |
| Hexanoic Acid | 1 | 1.31 |
| Formamide | 1 | 1.27 |
| Formamide, Ethylene glycol methyl ether | ½:½ | 1.34 |

TABLE 3

Data From Run Made In Rectification Column

| Agent | Column | Time, hrs. | Weight % Vinyl Acetate | Weight % Ethyl Acetate | Relative Volatility |
|---|---|---|---|---|---|
| Formic Acid-Formamide | Overhead | 0.5 | 89.3 | 10.7 | 1.52 |
| | Bottoms | | 47.4 | 52.6 | |
| Formic Acid-Formamide | Overhead | 1 | 90.9 | 9.1 | 1.60 |
| | Bottoms | | 45.2 | 54.8 | |

DETAILED DESCRIPTION OF THE INVENTION

I have discovered that certain carboxylic acids or acid amides, either alone or admixed with other high boiling organic compounds, will effectively increase the relative volatility of vinyl acetate to ethyl acetate and permit the separation of vinyl acetate from ethyl acetate by rectification when employed as the agent in extractive distillation. Table 2 lists the acids, acid amides and their mixtures and the approximate proportions that I have found to be effective. The data in Table 2 was obtained in a vapor-liquid equilibrium still. In each case, the starting material was a 50-50 wt.% mixture of vinyl acetate and ethyl acetate. The ratios are the parts by weight of extractive agent used per part of vinyl acetate-ethyl acetate mixture. The compounds which are effective are when used alone are formic acid, propionic acid, hexanoic acid and formamide. The compounds which are effective when used in mixtures are acetamide, acetophenone, adiponitrile, ethylene glycol methyl ether and sulfolane.

The relative volatilities shown in Table 2 were determined in a vapor-liquid equilibrium still. For example, in Table 2, one part of formic acid mixed with one part of the vinyl acetate-ethyl acetate mixture give a relative volatility of 1.58. One half part of formic acid mixed with one half part of formamide with one part of the vinyl acetate-ethyl acetate mixture gives a relative volatility of 1.72. In every example in Table 2, the starting material is a vinyl acetate-ethyl acetate mixture which possesses a relative volatility of 1.08.

TABLE 4

Potential Extractive Distillation Agents Which Are Ineffective

| Compounds | Ratio | Relative Volatility |
|---|---|---|
| Acetic acid | 1 | 1.10 |
| Neopentanoic acid | 1 | 1.15 |
| Heptanoic acid | 1 | 1.07 |
| Octanoic acid | 1 | 1.08 |
| Pelargonic acid | 1 | 1.08 |
| Formic acid - Dimethylformamide | ½:½ | 1.10 |
| Formic acid - Dimethylacetamide | ½:½ | 1.15 |

Table 4 lists several extractive distillation agents which might have been expected to be effective but which produced a relative volatility too low to be attractive.

One of the mixtures, formic acid-formamide, listed in Table 2 and whose relative volatility has been determined in the vapor-liquid equilibrium still, was then evaluated in a glass perforated plate rectification column possessing 5.3 theoretical plates and the results listed in Table 3. The data in Table 3 was obtained in the following manner. The charge was 200 grams of 50% vinyl acetate-50% ethyl acetate and after a half hour of operation in the 5.3 theoretical plate column to establish equilibrium, a mixture comprising 50% formic acid-50% formamide at 85° C. and 20 ml/min. was pumped in. The rectification was continued with sampling of overhead and bottoms after ½ hour. The analysis is shown in Table 3 and was 89.3% vinyl acetate, 10.7% ethyl acetate in the overhead and 47.4% vinyl acetate, 52.6% ethyl acetate in the bottoms which gives a relative volatility of 1.52 of vinyl acetate to ethyl acetate. After one hour of continuous operation, the overhead was 90.9% vinyl acetate, 9.1% ethyl acetate, the bottoms was 45.2% vinyl acetate, 54.8% ethyl acetate which is a relative volatility of 1.60.

THE USEFULNESS OF THE INVENTION

The usefulness or utility of this invention can be demonstrated by referring to the data presented in Tables 1, 2 and 3. All of the successful extractive distillation agents show that vinyl acetate and ethyl acetate can be separated from their mixtures by means of distillation in a rectification column and that the ease of separation as measured by relative volatility is considerable. Without these extractive distillation agents, little improvement will occur in the rectification column. The data also show that the most attractive agents will operate at a boilup rate low enough to make this a useful and efficient method of recovering high purity vinyl acetate from any mixture with ethyl acetate. The stability of the compounds used and the boiling point difference is such that complete recovery and recycle is obtainable by a simple distillation and the amount required for makeup is small.

WORKING EXAMPLES

Example 1: Fifty grams of a vinyl acetate-ethyl acetate mixture and 50 grams of formic acid were charged to a vapor-liquid equilibrium still and refluxed for two hours. Analysis indicated a vapor composition of 61.4% vinyl acetate, 38.6% ethyl acetate, a lquid composition of 47% vinyl acetate, 53% ethyl acetate which is a relative volatility of 1.79.

Example 2: Fifty grams of a vinyl acetate-ethyl acetate mixture, 25 grams of formic acid and 25 grams of formamide were charged to the vapor-liquid equilibrium still and refluxed for two hours. Analysis indicated a vapor composition of 64.8% vinyl acetate, 35.2% ethyl acetate, a liquid composition of 51.5% vinyl acetate, 48.5% ethyl acetate which is a relative volatility of 1.73.

Example 3: A glass perforated plate rectification column was calibrated with ethylbenzene and p-xylene which possesses a relative volatility of 1.06 and found to have 5.3 theoretical plates. A solution comprising 100 grams of vinyl acetate and 100 grams of ethyl acetate was placed in the stillpot and heated. When refluxing began, an extractive agent comprising 50% formic acid and 50% formamide was pumped into the column at a rate of 20 ml/min. The temperature of the extractive agent as it entered the column was 85° C. After establishing the feed rate of the extractive agent, the heat input to the vinyl acetate and ethyl acetate in the stillpot was adjusted to give a total reflux rate of 10–20 ml/min. After one half hour of operation, the overhead and bottoms samples of approximately two ml. were collected and analysed by gas chromatography. The overhead analysis was 89.3% vinyl acetate, 10.7% ethyl acetate. The bottoms analysis was 47.4% vinyl acetate, 52.6% ethyl acetate. Using these compositions in the Fenske equation, with the number of theoretical plates in the column being 5.3, gave an average relative volatility of 1.52 for each theoretical plate. After one hour of total operating time, the overhead and bottoms samples were again taken and analysed. The overhead composition was 90.9% vinyl acetate, 9.1% ethyl acetate and the bottoms composition was 45.2% vinyl acetate, 54.8% ethyl acetate. This gave an average relative volatility of 1.60 for each theoretical plate. These data are presented in Table 3.

I claim:

1. A method for recovering vinyl acetate from mixtures of vinyl acetate and ethyl acetate which comprises distilling a mixture of vinyl acetate and ethyl acetate in a rectification column in the presence of about one part of an extractive agent per part of vinyl acetate-ethyl acetate mixture, recovering vinyl acetate as overhead product and obtaining the ethyl acetate and the extractive agent from the stillpot, wherein said extractive agent comprises formic acid and one material selected from the group consisting of formamide, acetophenone, adiponitrile, sulfolane and acetamide.

2. A method for recovering vinyl acetate from mixtures of vinyl acetate and ethyl acetate which comprises distilling a mixture of vinyl acetate and ethyl acetate in a rectification column in the presence of about one part of an extractive agent per part of vinyl acetate-ethyl acetate mixture, recovering vinyl acetate as overhead product and obtaining the ethyl acetate and the extractive agent from the stillpot, wherein said extractive agent comprises a mixture of formamide and ethylene glycol methyl ether.

* * * * *